US012020806B2

(12) United States Patent
Samset et al.

(10) Patent No.: US 12,020,806 B2
(45) Date of Patent: Jun. 25, 2024

(54) METHODS AND SYSTEMS FOR DETECTING ABNORMALITIES IN MEDICAL IMAGES

(71) Applicant: GE Precision Healthcare LLC, Milwaukee, WI (US)

(72) Inventors: Eigil Samset, Oppegård (NO); David Bates, Waukesha, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 897 days.

(21) Appl. No.: 16/807,912

(22) Filed: Mar. 3, 2020

(65) Prior Publication Data
US 2021/0280298 A1 Sep. 9, 2021

(51) Int. Cl.
*G16H 30/40* (2018.01)
*A61B 5/055* (2006.01)
(Continued)

(52) U.S. Cl.
CPC ............ *G16H 30/40* (2018.01); *A61B 5/055* (2013.01); *A61B 6/032* (2013.01); *A61B 6/037* (2013.01); *A61B 6/5217* (2013.01); *A61B 8/463* (2013.01); *A61B 8/469* (2013.01); *A61B 8/5223* (2013.01); *G06N 3/045* (2023.01); *G06N 3/08* (2013.01); *G16H 15/00* (2018.01); *G16H 30/20* (2018.01); *G16H 50/20* (2018.01); *G16H 50/50* (2018.01); *G16H 70/20* (2018.01); *G16H 70/60* (2018.01); *A61B 6/5247* (2013.01); *A61B 8/4444* (2013.01); *A61B 8/5261* (2013.01)

(58) Field of Classification Search
None
See application file for complete search history.

(56) References Cited

U.S. PATENT DOCUMENTS 10,140,421 B1 * 11/2018 Bernard ............... A61B 6/563
2017/0286614 A1 * 10/2017 Morris ............... H04L 9/0833
(Continued)

FOREIGN PATENT DOCUMENTS

WO WO-2011064695 A2 * 6/2011 ........... G06F 19/321

OTHER PUBLICATIONS

Sethole, Khethiwe Margaret. "Interpretations of Chest X-Rays by Radiographers and General Practitioners at District Hospitals in the City of Tshwane." Order No. 30707218 University of Pretoria (South Africa), 2018. Ann Arbor: ProQuest. Web. Feb. 23, 2024. (Year: 2018).*

*Primary Examiner* — Lena Najarian
(74) *Attorney, Agent, or Firm* — McCoy Russell LLP

(57) ABSTRACT

Various methods and systems are provided for a medical imaging system. In one embodiment, a method comprises acquiring medical imaging data while executing a first imaging protocol, detecting a potential abnormality by evaluating the acquired medical imaging data with an artificial intelligence system, and outputting a first notification regarding the potential abnormality to a display, the first notification including an option to accept the first notification and an option to reject the first notification. In this way, an operator of an ultrasound imaging system may be alerted to a patient abnormality during a scan, thereby enabling the operator to further evaluate the potential abnormality without distracting the operator from controlling the medical imaging system.

13 Claims, 8 Drawing Sheets

(51) Int. Cl.
*A61B 6/00* (2006.01)
*A61B 6/03* (2006.01)
*A61B 8/00* (2006.01)
*A61B 8/08* (2006.01)
*G06N 3/045* (2023.01)
*G06N 3/08* (2023.01)
*G16H 15/00* (2018.01)
*G16H 30/20* (2018.01)
*G16H 50/20* (2018.01)
*G16H 50/50* (2018.01)
*G16H 70/20* (2018.01)
*G16H 70/60* (2018.01)

(56) References Cited

U.S. PATENT DOCUMENTS

| | | | |
|---|---|---|---|
| 2018/0101645 A1* | 4/2018 | Sorenson | G06F 21/6245 |
| 2019/0102878 A1* | 4/2019 | Zhang | G06N 3/0454 |
| 2020/0075144 A1* | 3/2020 | Nakatsugawa | G16H 10/40 |
| 2021/0052253 A1 | 2/2021 | Cadieu et al. | |

\* cited by examiner

METHODS AND SYSTEMS FOR DETECTING ABNORMALITIES IN MEDICAL IMAGES

FIELD

Embodiments of the subject matter disclosed herein relate to ultrasound imaging.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or other user may interact with the workstation or device to analyze the images displayed on and/or select from the plurality of user-selectable inputs.

BRIEF DESCRIPTION

In one embodiment, a method comprises acquiring medical imaging data while executing a first imaging protocol, detecting a potential abnormality by evaluating the acquired medical imaging data with an artificial intelligence system, and outputting a first notification regarding the potential abnormality to a display, the first notification including an option to accept the first notification and an option to reject the first notification. In this way, an operator of a medical imaging system, such as an ultrasound imaging system, may be alerted to a patient abnormality during a scan, thereby enabling the operator to further evaluate the potential abnormality without distracting the operator from controlling the medical imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
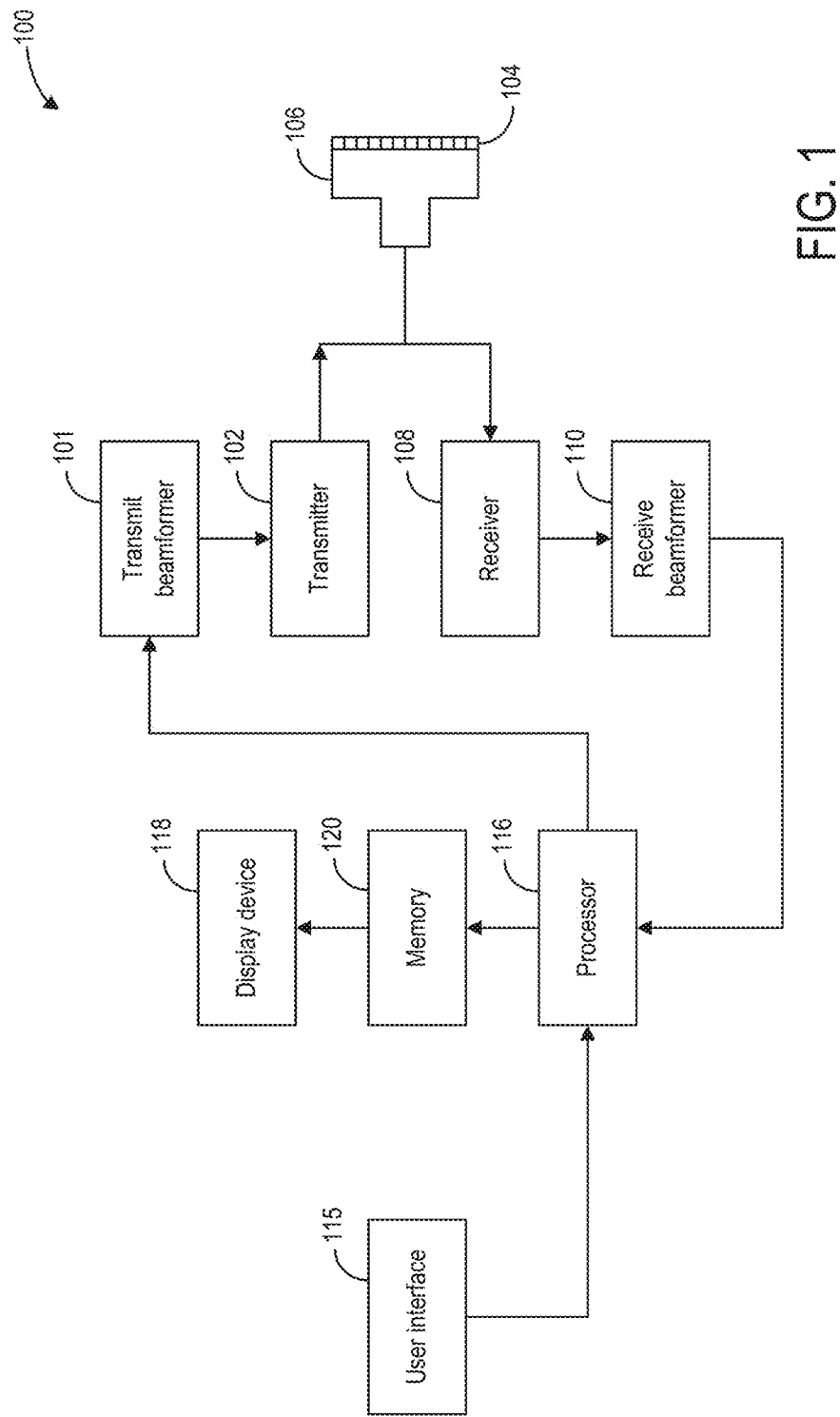
FIG. 1 shows a block schematic diagram of an ultrasound imaging system, according to an embodiment.
Figure 2:
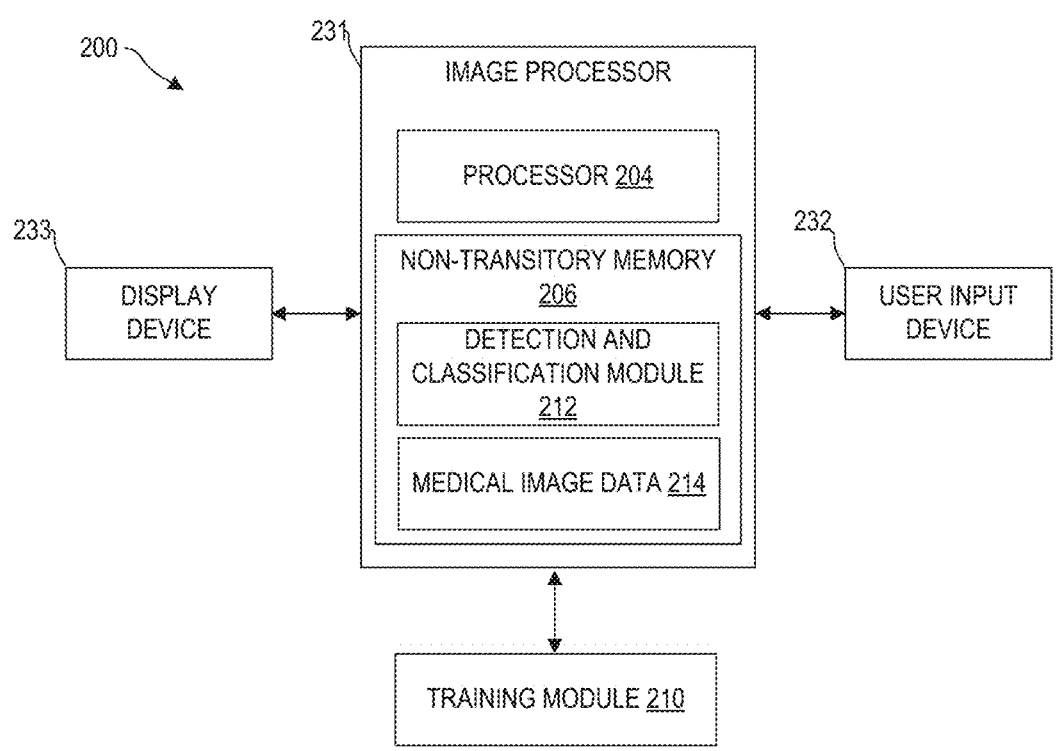
FIG. 2 is a schematic diagram illustrating an image processing system for detecting and classifying abnormalities in medical images, according to embodiment.

The following description relates to various embodiments of an imaging system, such as the ultrasound imaging system shown in FIG. 1. In particular, systems and methods are provided for automatically detecting potential physical (e.g., anatomical/pathological) or physiological (e.g., functional/dysfunctional) abnormalities in a patient based on medical imaging data and notifying an operator of the detected potential abnormality. As the processes described herein may be applied to pre-processed imaging data and/or to processed images, the term "image" is generally used throughout the disclosure to denote both pre-processed and partially-processed image data (e.g., pre-beamformed RF or I/Q data, pre-scan converted RF data) as well as fully processed images (e.g., scan converted and filtered images ready for display). An example image processing system that may be used to detect the potential abnormalities is shown in FIG. 2. The image processing system may employ image processing and deep learning algorithms to detect the potential abnormality and output one or more notifications regarding the detected potential abnormality to the operator, such as according to the method of FIGS. 3A-3C. As depicted by the example display outputs in FIGS. 4A-4E, the one or more notifications may be user-centric in their positioning and in their prompts. Further, the one or more notifications may include patient-centric information. In this way, abnormalities may be detected from ultrasound imaging data even while the patient is not initially examined for such abnormalities.

Advantages that may be realized in the practice of some embodiments of the described systems and techniques are that inconsistencies in the detection of abnormalities, particularly between different operators, may be decreased. This may be particularly advantageous for increasing a detection accuracy of point-of-care ultrasound operators, who may have less training than ultrasound experts (e.g., sonographers, radiologists, or cardiologists). For example, an emergency room physician, who may not receive expert-level ultrasound training, may be more likely to overlook an abnormality or incorrectly identify a normal structure or an imaging artifact as an abnormality, which may increase a burden on a radiology or cardiology department for follow up scans and increase patient discomfort. Further, when the potential abnormality is detected from data obtained during a scan while the scan is still being performed, the one or more notifications may include guidance for adapting the scan to verify the potential abnormality. The guidance may include suggestions for acquiring additional views using a current ultrasound protocol/imaging mode or for acquiring additional views using a different ultrasound protocol/imaging mode that would not be performed otherwise. As a result, the one or more notifications may provide feedback that is specific to the patient being examined and the type of potential abnormality detected. Further still, the one or more notifications may be presented to the operator in a manner that does not distract the operator or disrupt the exam being performed. As a result, operator disturbance may be decreased.

Although the systems and methods described below for evaluating medical images are discussed with reference to an ultrasound imaging system, it may be noted that the methods described herein may be applied to a plurality of imaging systems (e.g., MRI, PET, x-ray, or other similar systems).

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives elements (e.g., transducer elements) 104 within a transducer array, herein referred to as a probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system. In one embodiment, data acquired via the ultrasound imaging system 100 may be used to train a machine learning model, as will be elaborated below with respect to FIG. 2.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus, the display device 118 may be included in the user interface 115.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, elastography, tissue velocity imaging, strain, strain rate, and the like) to form 2D or three-dimensional (3D) images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain, strain rate, and the like, and combinations thereof. As one example, the one or more modules may process color Doppler data, which may include traditional color flow Doppler, power Doppler, high-definition (HD) flow Doppler, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real-time while a procedure (e.g., ultrasound imaging) is being performed on a patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), an MRI system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a field-programmable gate array (FPGA), or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a detection and classification module 212 and medical image data 214. The detection and classification module 212 includes one or more artificial intelligence algorithms, including machine learning models, to process input medical images from the medical image data 214. Specifically, the detection and classification module 212 may provide an artificial intelligence system for identifying patient abnormalities within the medical image data 214. For example, the detection and classification module 212 may include one or more deep learning networks comprising a plurality of weights and biases, activation functions, loss functions, gradient descent algorithms, and instructions for implementing the one or more deep learning networks to process input medical images. Additionally or alternatively, the detection and classification module 212 may store instructions for implementing a neural network, such as a convolutional neural network, for detecting and classifying potential patient abnormalities captured in the medical image data 214. The detection and classification module 212 may include trained and/or untrained neural networks and may further include training routines, or parameters (e.g., weights and biases), associated with one or more neural network models stored therein. The detection and classification module 212 may further include image recognition algorithms, shape or edge detection algorithms, and the like. In some embodiments, the detection and classification module 212 may evaluate the medical image data 214 as it is acquired in real-time. Additionally or alternatively, the detection and classification module 212 may evaluate the medical image data 214 offline, not in real-time.

In some embodiments, the potential patient abnormalities may include abnormal growth or pathologies in an anatomical feature imaged in the medical image data 214. For example, when the anatomical feature is the heart, the patient abnormalities may include a vegetation, a thrombus, abnormal (e.g., reduced or increased) motion, abnormal flow velocities, enlargement of a heart chamber (e.g., an atrium or ventricle), and/or abnormal stroke volume, as will be elaborated below with respect to FIGS. 3A-3C. Thus, the potential patient abnormalities include anatomical abnormalities and foreign masses as well as abnormal functionality of the anatomical feature. Herein, the abnormality is referred to as "potential" until otherwise verified by an operator or other clinician.

The image processor 231 may be communicatively coupled to a training module 210, which includes instructions for training one or more of the machine learning models stored in the detection and classification module 212. The training module 210 may include instructions that, when executed by a processor, cause the processor to build a model (e.g., a mathematical model) based on sample data to make predictions or decisions regarding the detection and classification of patient abnormalities without the explicit programming of a conventional algorithm that does not utilize machine learning. In one example, the training module 210 includes instructions for receiving training data sets from the medical image data 214. The training data sets comprise sets of medical images, associated ground truth labels/images, and associated model outputs for use in training one or more of the machine learning models stored in the detection and classification module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely-accessible networked storage devices configured in a cloud computing configuration. Further, in some embodiments, the training model 210 is included in the non-transitory memory 206. Additionally or alternatively, in some embodiments, the training model 210 may be used to generate the detection and classification module 212 offline and remote from the image processing system 200. In such embodiments, the training module 210 may not be included in the image processing system 200 but may generate data stored in the image processing system 200. For example, the detection and classification module 212 may be pre-trained with the training model 210 at a place of manufacture.

The non-transitory memory 206 further stores the medical image data 214. The medical image data 214 includes, for example, functional and/or anatomical images captured by an imaging modality, such as ultrasound imaging systems, MRI systems, CT systems, PET systems, etc. As one example, the medical image data 214 may include ultrasound images, such as cardiovascular ultrasound images. Further, the medical image data 214 may include one or more of 2D images, 3D images, static single frame images, and multi-frame cine-loops (e.g., movies).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231. As an example, the user input device 232 may enable a user to analyze and rank imaged structures and/or respond to notification prompts.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without parting from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3A:
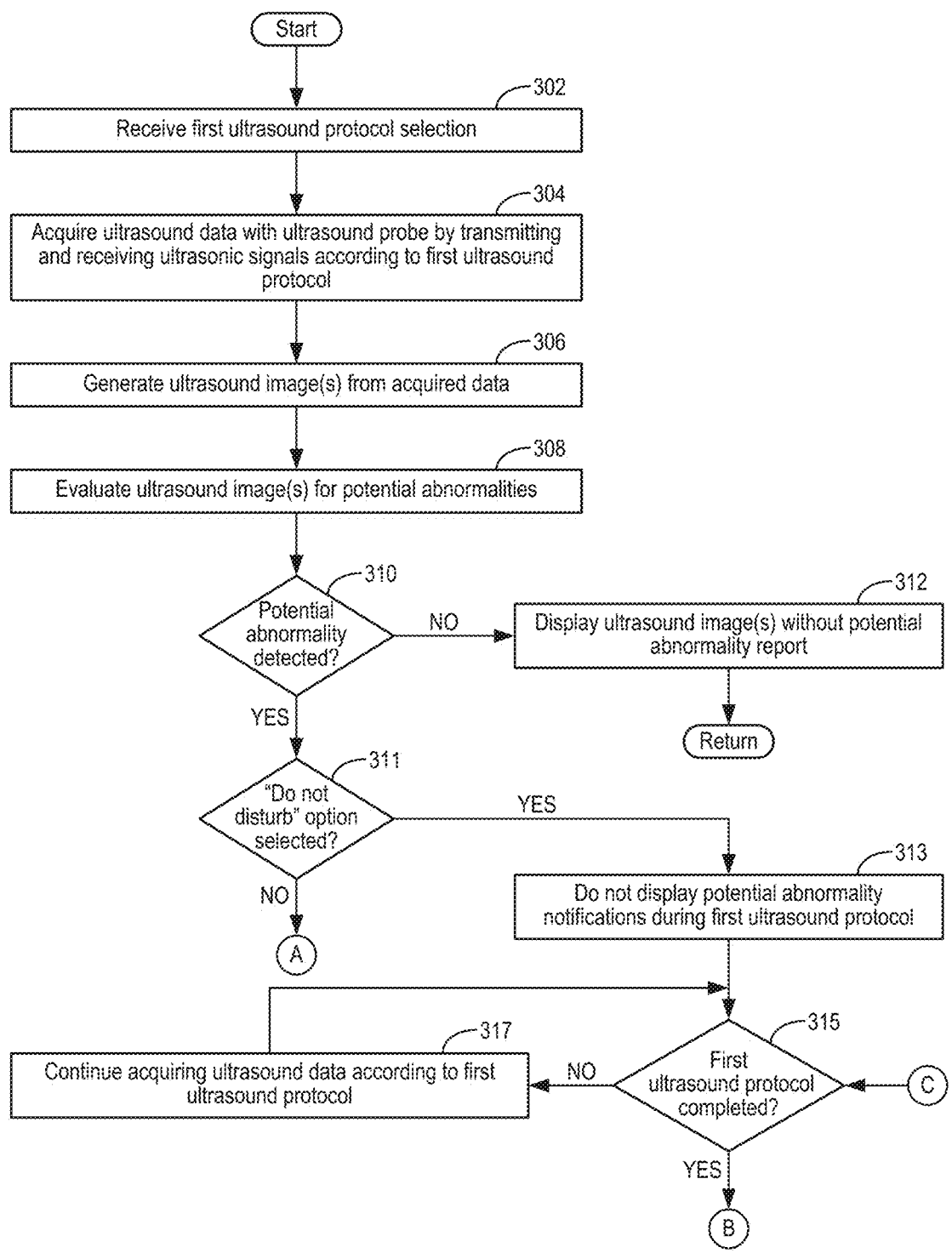
FIGS. 3A-3C show a flow chart of an example method for detecting a potential abnormality in an ultrasound image and outputting a notification regarding the potential abnormality, according to an embodiment.
Figure 3B:
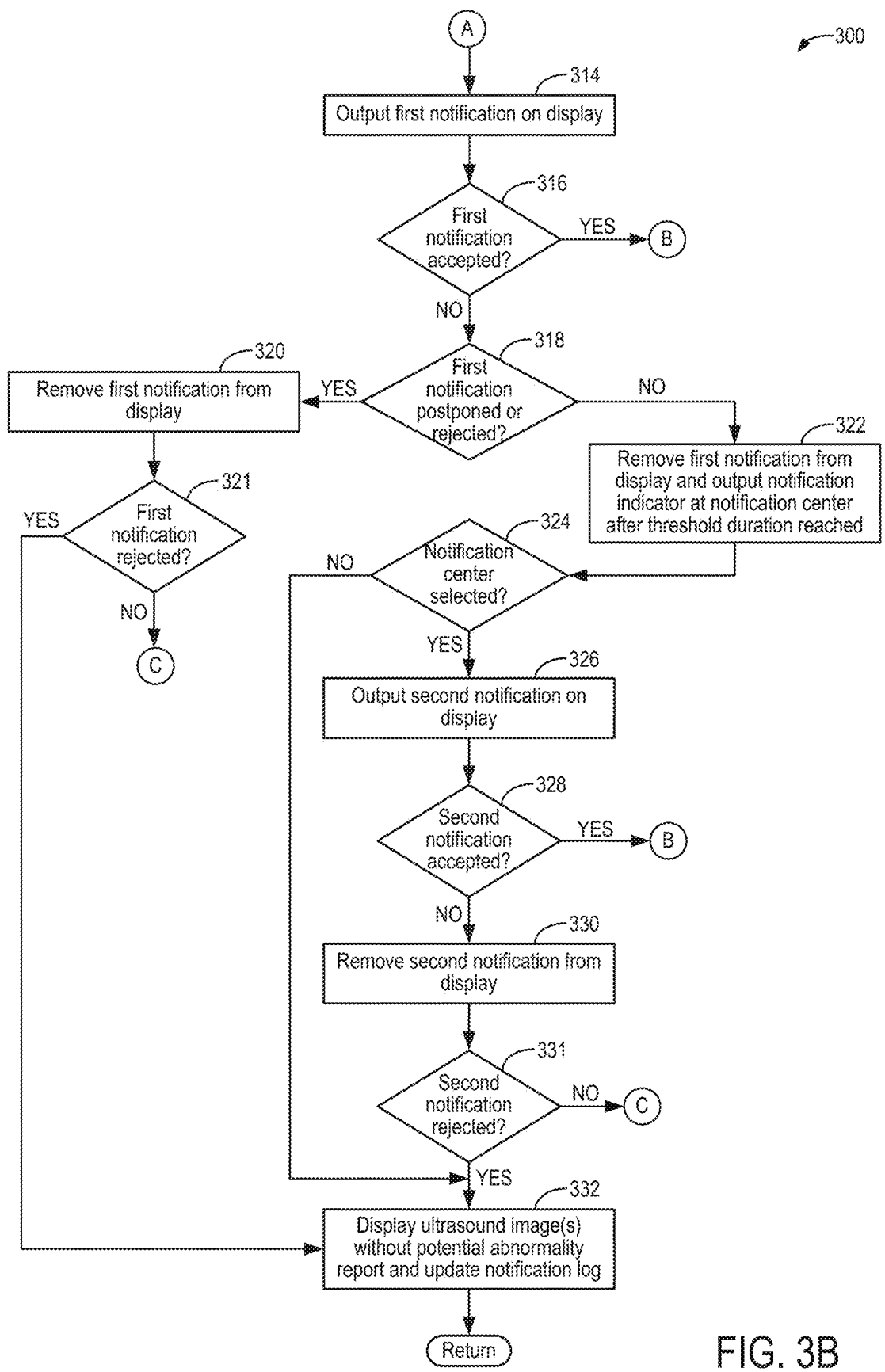
Figure 3C:
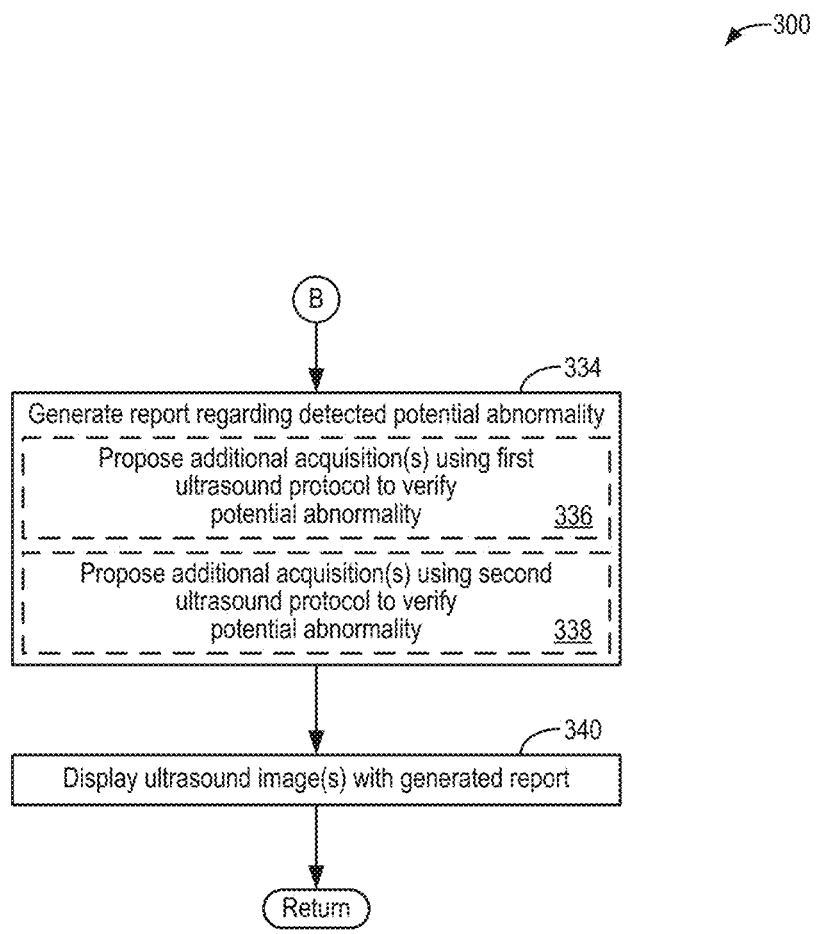

FIGS. 3A-3C show an example method 300 for detecting a potential abnormality in medical images and outputting an alert for verifying the potential abnormality. In particular, method 300 provides a workflow for expediting and increasing an accuracy of detecting and characterizing an abnormality of an anatomical feature of a patient. Method 300 will be described for ultrasound images acquired using an ultrasound imaging system, such as ultrasound imaging system 100 of FIG. 1, although other ultrasound imaging systems may be used. Further, method 300 may be adapted to other imaging modalities. Method 300 may be implemented by one or more of the above described systems, including the ultrasound imaging system 100 of FIG. 1 and medical image processing system 200 of FIG. 2. As such, method 300 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, method 300 is performed in real-time, as the ultrasound images are acquired, while in other embodiments, at least portions of method 300 are performed offline, after the ultrasound images are acquired. For example, the processor may evaluate ultrasound images that are stored in memory even while the ultrasound system is not actively being operated to acquire images. Further still, at least parts of method 300 may be performed in parallel. For example, ultrasound data for a second image may be acquired while a first ultrasound image is generated, ultrasound data for a third image may be acquired while the first ultrasound image is evaluated for potential abnormalities, and so on.

At 302, method 300 includes receiving a first ultrasound protocol selection. The first ultrasound protocol may be selected by an operator (e.g., user) of the ultrasound imaging system via a user interface (e.g., the user interface 115). As one example, the operator may select the first ultrasound protocol from a plurality of possible ultrasound protocols using a drop-down menu or by selecting a virtual button. Alternatively, the system may automatically select the protocol based on data received from an electronic health record (EHR) associated with the patient. For example, the EHR may include previously performed exams, diagnoses, and current treatments, which may be used to select the first ultrasound protocol. Further, in some examples, the operator may manually input and/or update parameters to use for the first ultrasound protocol. The first ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the first ultrasound protocol may include a plurality of views and/or imaging modes that are sequentially performed. Using cardiac ultrasound imaging as an example, the first ultrasound protocol may include a four-chamber view of the left ventricle with B-mode, a four-chamber view of the left ventricle with color flow imaging (CFI), a four-chamber view with a Doppler spectrum of mitral inflow, a two-chamber view, an apical long axis view (APLAX), APLAX with CFI, a parasternal long axis view (PLAX), PLAX with CFI, and a four-chamber view focused on the right ventricle.

At 304, method 300 includes acquiring ultrasound data with an ultrasound probe by transmitting and receiving ultrasonic signals according to the first ultrasound protocol. In the above cardiac ultrasound imaging example, performing the first ultrasound protocol includes acquiring ultrasound data for some or all of the above-mentioned views and imaging modes. Acquiring ultrasound data according to the first ultrasound protocol may include the system displaying instructions on the user interface, for example, to guide the operator through the acquisition of the designated views. Additionally or alternatively, the first ultrasound protocol may include instructions for the ultrasound system to automatically acquire some or all of the data or perform other functions. For example, the first ultrasound protocol may include instructions for the user to move, rotate and/or tilt the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or ultrasound signal display parameters. Further, the acquired ultrasound data include one or more image parameters calculated for each pixel or group of pixels (for example, a group of pixels assigned the same parameter value) to be displayed, where the one or more calculated image parameters include, for example, one or more of an intensity, velocity, color flow velocity, texture, graininess, contractility, deformation, and rate of deformation value.

At 306, method 300 includes generating ultrasound image(s) from the acquired ultrasound data. At least one ultrasound image may be generated for each view of the first ultrasound protocol. For example, the signal data acquired during the method at 304 is processed and analyzed by the processor in order to produce an ultrasound image. The processor may include an image processing module that receives the signal data (e.g., image data) acquired at 304 and processes the received image data. For example, the image processing module may process the ultrasound signals to generate slices or frames of ultrasound information (e.g., ultrasound images) for displaying to the operator. In one example, generating the image may include determining an intensity value for each pixel to be displayed based on the received image data (e.g., 2D or 3D ultrasound data). As such, the generated ultrasound images may be 2D or 3D depending on the mode of ultrasound being used (e.g., CFI, acoustic radiation force imaging, B-mode, A-mode, M-mode, spectral Doppler, acoustic streaming, tissue Doppler module, C-scan, or elastography).

At 308, method 300 includes evaluating the ultrasound image(s) for potential abnormalities. As used herein, the term "abnormalities" refers to physical and physiological features or parameters that are outside of a standardized range, pathological, and/or uncharacteristic of the patient being scanned. Continuing with the above cardiac ultrasound imaging example, the potential abnormalities may include a vegetation (e.g., bacterial growth), tumor (e.g. cancerous tissue), thrombus (e.g., blood clot), abnormal anatomy, abnormal motion, abnormal blood flow, and abnormal blood volume. Examples of abnormal anatomy include enlargement of an atrium or ventricle, thickening of a wall, etc. Examples of abnormal motion include reduced or increased motion. Examples of abnormal blood flow include abnormally high or low blood flow velocities with respect to a standardized blow flow velocity range and/or backflow through a closed valve. Examples of abnormal blood volume include reduced or increased blood stroke volume.

Evaluating the ultrasound image(s) for potential abnormalities includes using an artificial intelligence system to identify and characterize features viewable in one or more ultrasound images, such as by using one or more algorithms. As an example, the artificial intelligence system may include detection and classification module 212 of FIG. 2. The artificial intelligence system may be trained to identify and quantify features that are normally present in particular views as well as features that are not normally present in particular views, such as a vegetation or thrombus. For example, the artificial intelligence system may include object detection and segmentation algorithms for identifying features (such as chambers, valves, vegetations, etc.) as well as measurement automation algorithms for quantifying the features (dimensions, velocities, volumes, etc.). Further, the artificial intelligence system may employ machine learning in order to continuously or periodically update training data and increase an accuracy of the detection.

The artificial intelligence system may compare the feature quantifications with standardized ranges used for all patients or patients of a similar size, age, and gender as well as with patient-specific data, if available. The patient-specific data may include data from previous scans acquired via ultrasound or other imaging modalities as well as data acquired during the current scan. As an example, a significant difference in stroke volume between the left ventricle and right ventricle indicates a potential blood flood and/or blood volume abnormality. As used herein, "significant difference" may refer to a statistically significant difference or a difference that is greater than a pre-defined threshold difference for a given parameter. As another example, reduced motion in one portion of the heart relative to other portions of the heart acquired in the same or different views may indicate potential abnormal motion. Thus, the artificial intelligence system may evaluate each generated ultrasound image alone and in combination with other ultrasound images acquired during the scan to identify potential abnormalities.

Further still, the artificial intelligence system may evaluate the ultrasound image(s) for any possible potential abnormality in the views received regardless of an intent of the selected first ultrasound protocol or a current patient diagnosis and without input from the operator. For example, the first ultrasound protocol may be a stress echocardiogram protocol intended to visualize motion of the heart's walls and pumping action to assess blood flow when the heart is stressed. During such stress echocardiogram, the artificial intelligence system may be trained to identify vegetations and/or a plurality of other potential abnormalities, such as those described above, and may be further trained on which view or combination of views to evaluate for each of the plurality of potential abnormalities even though such abnormality identification is not the primary or intended purpose of the selected first ultrasound protocol. Thus, upon generating or otherwise obtaining a view or combination of views that fit criteria for determining the presence or absence of a particular potential abnormality, the artificial intelligence system automatically evaluates the view or combination of views for that potential abnormality. The artificial intelligence system may detect which view is represented in each ultrasound image based on the ultrasound image itself (e.g., using image recognition) or based on the selected first ultrasound protocol.

At 310, method 300 includes determining if a potential abnormality is detected. A potential abnormality is detected if at least one potential abnormality is identified while evaluating the ultrasound image(s) for potential abnormalities at 308. Conversely, a potential abnormality is not detected if no potential abnormalities are identified by the artificial intelligence system at 308.

If a potential abnormality is not detected (e.g., no potential abnormalities are identified at 308), method 300 proceeds to 312 and includes displaying the ultrasound image(s). Displaying the ultrasound image(s) includes outputting the generated ultrasound image(s) on a display device. For example, the pixel parameter values calculated at 306 comprise the displayed image(s) output to the display device. In some examples, the display device is included in the ultrasound imaging system, such as display device 118. Further, because no potential abnormality has been detected, information and prompts regarding potential abnormalities will not be generated. Following 312, method 300 returns. As an example, method 300 may be repeated until the first ultrasound protocol is completed (e.g., finished).

If instead a potential abnormality is detected at 310, method 300 proceeds to 311 and includes determining if a "do not disturb" option is selected. The "do not disturb" option is a notification setting that, when selected, prevents information about detected potential abnormalities from being displayed until the first ultrasound protocol is completed. As a result, the operator will not be disturbed while performing the first ultrasound protocol, allowing the operator to focus on the exam without increased distraction from pop-up notifications. As an example, the operator may switch the "do not disturb" option between an "on" state, where the "do not disturb" option is selected, and an "off" state, where the "do not disturb" option is not selected, via a user input device. The user input device may be included in the user interface used to select the first ultrasound protocol or may be included in a separate user interface. The user input device may include one or more of a mouse, touchpad, touchscreen, stylus, hard key system, and microphone (e.g., for a voice command system). Selecting the "do not disturb" option may include the operator performing a pre-defined selection action using the user input device (such as clicking, tapping, swiping, or the like) at a corresponding icon, check box, or virtual toggle switch, for example. Additionally or alternatively, selecting the "do not disturb" option may include the operator communicating a pre-determined voice command for selecting the "do not disturb" option to the voice command system or depressing a hard key pre-programmed for selecting the "do not disturb" option. In each example, the processor may determine that the "do not disturb" option is selected responsive to receiving a corresponding input to switch the "do not disturb" option to the "on" state.

In some examples, the selected first ultrasound protocol includes a default setting for the "do not disturb" option. For example, upon selection of the first ultrasound protocol, the "do not disturb" option may be automatically switched "on" or "off" depending on the default setting stored with the first ultrasound protocol. As an illustrative example, when the first ultrasound protocol is the stress echocardiogram protocol described above, the "do not disturb" option may be automatically switched to the "on" state to reduce operator distraction. Additionally or alternatively, the operator may program a default "do not disturb" setting that may be automatically selected upon the operator logging into the ultrasound imaging system. However, in each example, the operator may choose to switch the "do not disturb" option from the default setting associated with the first ultrasound protocol and/or the operator. Further, the operator may switch the "do not disturb" option between the "on" state and the "off" state at any point and multiple times during the scan.

Additionally or alternatively, in some examples, the processor may automatically select the "do not disturb" option while the first ultrasound protocol is being executed responsive to a threshold number of notification rejections and/or postponements being received during the first ultrasound protocol. The threshold number of notification rejections and/or postponements refers to a pre-determined, non-zero number of notification rejections and postponements that suggests that the operator does not agree with the detected potential abnormalities (e.g., notification rejections) or is not currently available to verify the detected potential abnormalities (e.g., notification postponements). For example, the operator may indirectly select the "do not disturb" option by continually rejecting and/or postponing output potential abnormality notifications without accepting any of the notifications. Rejecting, postponing, and accepting the potential abnormality notifications will be elaborated below. For example, the "do not disturb" option may function to automatically postpone and/or silence notifications for each potential abnormality detected while the "do not disturb" function is turned "on" without the notifications being displayed or the operator interacting with the notifications.

If the "do not disturb" option is selected, method 300 proceeds to 313 and includes not displaying potential abnormality notifications during the first ultrasound protocol. Thus, while the first ultrasound protocol is being executed and the "do not disturb" option is selected, pop-up notifications regarding the potential abnormality will be silenced, although notification content may be generated and stored at a notification log that will be further described below with respect to 332. For example, even when the notifications are not presented to the operator, the notification log stores the information that would otherwise be displayed to the operator.

At 315, method 300 includes determining if the first ultrasound protocol is completed. The first ultrasound protocol may be considered completed when ultrasound data is acquired for all of the views and/or imaging modes programmed in the first ultrasound protocol and the ultrasound probe is no longer actively transmitting and receiving ultrasonic signals according to the first ultrasound protocol. Additionally or alternatively, the first ultrasound protocol may be considered completed responsive to the processor receiving an "end protocol" input from the operator.

If the first ultrasound protocol is completed, method 300 proceeds to 334 (see FIG. 3C) and includes generating a report regarding the detected potential abnormality. As will be elaborated below, the generated report includes a suggested action for verifying (e.g., confirming) the potential abnormality. In some examples, the suggested action includes proposing additional acquisition(s) using the first ultrasound protocol to verify the potential abnormality, as optionally indicated at 336. In other examples, the suggested action additionally or alternatively includes proposing additional acquisition(s) using a second ultrasound protocol to verify the potential abnormality, as optionally indicated at 338. Thus, the system may delay generating and outputting the report regarding any potential abnormalities detected while the "do not disturb" option is selected until the first ultrasound protocol is completed, and the system may further automatically generate and output the report responsive to the first ultrasound protocol being completed.

If the first ultrasound protocol is not completed, such as when the ultrasound probe is still actively acquiring ultrasound data according to the first ultrasound protocol and/or there are remaining views/imaging modes in the first ultrasound protocol, method 300 proceeds to 317 and includes continuing to acquire ultrasound data according to the first protocol. As such, the operator will not be prompted to further evaluate or verify the detected potential abnormality while the first ultrasound protocol is being performed.

Returning to 311, if the "do not disturb" option is not selected, method 300 proceeds to 314 (see FIG. 3B) and includes outputting a first notification on a display. The display may be the display device included in the ultrasound imaging system and used for displaying the ultrasound image or may be a different display device (e.g., display device 233 of FIG. 2). For example, the display may be included in a smartphone, a smartwatch, a tablet, or the like that is communicatively coupled to the ultrasound imaging system. The first notification includes information regarding the detected potential abnormality, such as an identity and location of the potential abnormality (e.g., a potential thrombus in the left atrium). The first notification may not include quantification information, annotated images of the potential abnormality, or propose additional actions for verifying the potential abnormality, at least in some examples. Thus, a reduced amount of information may be included in the first notification (e.g., relative to the report, as will be further elaborated below) in order to reduce operator distraction. When more than one potential abnormality is detected, separate first notifications may be generated for each of the detected potential abnormalities.

The first notification also prompts the operator to accept, postpone, or reject the notification, and thus a verification process for the detected potential abnormality, via an accept icon, a postpone icon, and a reject icon, respectively. As will be elaborated below with respect to FIG. 4B, the accept, postpone, and reject icons may each comprise a selectable virtual button having a defined image or symbol at a defined location on the display. Further, the first notification may be positioned to avoid disturbing the operator or obscuring information and controls for performing the ultrasound scan (e.g., the first ultrasound protocol). Additionally or alternatively, the first notification may be at least partially positioned adjacent the detected abnormality. The first notification may be a pop-up message and may include subtle motion effects or other animation to draw attention without distracting the operator. In some examples, outputting the first notification on the display may coincide with outputting an audible notification, such as a chime or other notification sound.

The first notification is output automatically, without instruction from the operator. In some examples, the first notification may be output as soon as the potential abnormality is detected, without intended delay. In other examples, the first notification output may be strategically delayed so that the first notification is output during a time that is expected to reduce disturbance to the operator while increasing visibility of the first notification. For example, the first notification may be output between views, while the ultrasound probe is not active, or during other breaks in the protocol.

At 316, method 300 includes determining if the first notification is accepted. The operator may accept the first notification by indicating acceptance via the user input device. Indicating acceptance may include the operator selecting the accept icon by positioning a cursor controlled by the user input device at the defined location for the accept icon and performing a pre-defined selection action (such as clicking, tapping, or the like). Additionally or alternatively, indicating acceptance may include the operator communicating a pre-determined voice command for accepting the first notification to the voice command system or depressing a hard key pre-programmed for accepting the first notification. In each example, the processor may determine that the first notification is accepted responsive to receiving a corresponding "accept" input. If the first notification is accepted, method 300 proceeds to 334 (see FIG. 3C) and includes generating the report regarding the detected potential abnormality. For example, the report may be instantaneously generated (e.g., immediately and without intentional delay) upon receiving acceptance of the first notification, in contrast to delaying the report generation until the first ultrasound protocol is completed (e.g., as when the first notification is silenced via the "do not disturb" option or postponed). In some examples that will be further elaborated herein, when the first notification is accepted, the system may temporarily pause the first ultrasound protocol to propose or initiate additional views in the first ultrasound protocol and/or the second ultrasound protocol, which are designed to evaluate the potential abnormality, via the report. After the additional views and/or the second ultrasound protocol are performed, the first protocol resumes from where it left off.

If the first notification is not accepted, method 300 proceeds to 318 and includes determining if the first notification is postponed or rejected. The operator may postpone or reject the first notification by indicating postponement or rejection via the user input device in the manner described above at 316 for accepting the first notification. For example, the operator may indicate postponement or rejection of the first notification to the processor by selecting the postpone or reject icon, respectively, via a pre-determined voice command for postponing or rejecting the first notification, or via a hard key pre-programmed for postponing or rejecting the notification. Thus, the processor may determine that the first notification is postponed or rejected responsive to receiving a "postpone" or "reject" input, respectively.

If the first notification is postponed or rejected, method 300 proceeds to 320 and includes removing the first notification from the display. If the first notification is postponed, the operator will not be further prompted to verify the detected potential abnormality until the first protocol is fully completed. If the first notification is rejected, by contrast, the operator will not be further prompted to interact with the first notification and will not receive any other notifications about the detected potential abnormality even after the first protocol is completed. In either case, however, if additional potential abnormalities are subsequently detected, first notifications regarding the additional potential abnormalities will be generated and displayed to the operator with the same accept, postpone, and reject options as described above.

At 321, method 300 includes determining if the first notification is rejected. As mentioned above, while the first notification will be removed from the display responsive to either the first notification being postponed or the first notification being rejected, postponement and rejection produce different results upon completion of the first ultrasound protocol. Therefore, postponement of the first notification and rejection of the first notification are distinguished from one another at 321.

If the first notification is not rejected (e.g., the first notification is postponed), method 300 proceeds to 315 (see FIG. 3A) and includes determining if the first ultrasound protocol is completed, as elaborated above. In contrast, if the first notification is rejected, method 300 proceeds to 332 and includes displaying the ultrasound image(s) without a potential abnormality report and updating the notification log. Details regarding the potential abnormality will not be displayed with or stored with the ultrasound image(s), and the ultrasound image(s) may be displayed on the display device as described above at 312. However, the notification log may store all incidences of potential abnormality detection, including exam identifiers (e.g., date, time, file name), the view(s) used to detect the potential abnormality, the potential abnormality type and quantifiers, and whether the associated notification was silenced (e.g., via the "do not disturb" option being selected), accepted, postponed, or rejected. In some examples, the notification log may be used to increase an accuracy of the potential abnormality detection. For example, the processor may use the notification log to identify repeated rejections for particular types of potential abnormalities or those identified in particular views/combinations of views and may use this information for further training of the artificial intelligence system. As another example, a supervisor may access and review the notification log for operator training purposes. In still another example, if the operator rejects the first notification in error, the operator may access the notification log to restore the information given in the first notification, including the option to accept the first notification. Further, the operator (or other user) may select a notification log entry and view the associated report (e.g., if the notification was not rejected) and be presented an option to perform the suggested action for verifying the potential abnormality. Further still, the notification log may include a filtering option so that the operator or other user may filter accepted/rejected/postponed/silenced notifications in the notification log, filter by the type of abnormality detected, etc. Method 300 may then return.

Returning to 318, if the first notification is not postponed or rejected, method 300 proceeds to 322 and includes removing the first notification from the display and outputting a notification indicator at a notification center after a threshold duration is reached. As will be elaborated below with respect to FIGS. 4A-4E, the notification center may be represented on the display as a notification center icon comprising a selectable virtual button having a defined image or symbol at a defined location on the display. The notification indicator may include a counter, an alert symbol, or the like positioned at the notification center icon.

The threshold duration refers to a pre-determined time duration for displaying the first notification and allowing the operator to react to the first notification (e.g., by accepting, postponing, or rejecting the first notification) before the first notification is no longer displayed. In one example, the threshold duration is a time duration within a range from 3 to 8 seconds. For example, the threshold duration may be 4 seconds. In other examples, the threshold duration is shorter than 3 seconds or longer than 8 seconds. Further, once the threshold duration is reached and the first notification is removed, the operator may no longer have the option to interact with the first notification. However, the information conveyed in the first notification is stored at the notification center as a second notification, and the notification indicator indicates that at least one (second) notification is ready for further review. For example, the notification center may store the second notification for the detected potential abnormality along with notifications for any other potential abnormalities that have not been accepted, postponed, or rejected. Further, the second notification may not be automatically output to the display, but may be output upon selection of the notification center, as will be elaborated below at 326. By removing the first notification from the display after the threshold duration is reached, operator distraction may be decreased, particularly when more than one potential abnormality is detected during a scan.

At 324, method 300 includes determining if the notification center is selected. The operator may select the notification center via the user input device, similar to the manner described above for accepting the first notification at 316. For example, the operator may select the notification center by selecting the notification center icon (e.g., via a cursor controlled by a mouse, touchpad, touchscreen, or stylus), via a pre-determined voice command for selecting the notification center, or via a hard key pre-programmed for selecting the notification center. Thus, the processor may determine that the notification center is selected responsive to receiving a corresponding input.

If the notification center is not selected, method 300 proceeds to 332, as described above. Further, the notification indicator is not removed from the notification center so that the operator is reminded to open the notification center. Thus, the operator may choose when to review the notifications stored in the notification center.

If the notification center is selected at 324, method 300 proceeds to 326 and includes outputting a second notification on the display. The second notification includes at least the information provided in the first notification, such as the identity and location of the potential abnormality. In some examples, the second notification may include additional information that is not included in the first notification, such as the view(s) in which the potential abnormality was detected. However, the second notification may not include quantification information, annotated images of the potential abnormality, or propose additional actions for verifying the potential abnormality, at least in some examples. When more than one potential abnormality has not yet been addressed or was postponed via the corresponding first notification, separate second notifications may be output for each of the detected potential abnormalities. In some examples, selecting the notification center enables the operator to browse through a plurality of stored notifications and select which one to address first and/or to apply filters to show only the abnormalities that were postponed or not show abnormalities that were rejected while still showing the accepted and postponed abnormalities, all of which may be output as the second notification. Thus, unlike the first notification, which is output automatically responsive to detecting the potential abnormality, the second notification is output responsive to a received input (e.g., the selection of the notification center by the operator and/or the selection of that particular notification at the notification center). The second notification also prompts the operator to accept, postpone, or reject the notification via an accept icon, a postpone icon, and a reject icon, respectively, as described above for the first notification at 314.

At 328, it is determined if the second notification is accepted. The operator may accept the second notification by indicating acceptance via the user input device in the manner described above at 316. Thus, the processor may determine that the second notification is accepted responsive to receiving an "accept" input, such as receiving selection of the accept icon, receiving a pre-determined voice command for accepting the second notification, or via depression of a hard key pre-programmed for accepting the second notification.

If the second notification is not accepted, method 300 proceeds to 330 and includes removing the second notification from the display. Unlike the first notification, which is removed from the display after the threshold duration is reached if not accepted, postponed, or rejected, the second notification may remain on the screen until accepted, postponed, or rejected. Therefore, not accepting the notification includes postponing or rejecting the notification. The processor may determine that the second notification is postponed or rejected responsive to receiving a "reject" or "postpone" input, respectively, such as receiving selection of the postpone or reject icon, receiving a pre-determined voice command for postponing or rejecting the second notification, or via depression of a hard key pre-programmed for postponing or rejecting the second notification. Thus, responsive to the second notification being postponed or rejected, the system no longer prompts the operator to interact with the second notification or further review the detected potential abnormality during the first protocol.

At 331, method 300 includes determining if the second notification is rejected. If the second notification is rejected, method 300 proceeds to 322. As described above, the ultrasound image(s) may be displayed without a report regarding the potential abnormality. Further, the notification log may be updated. If the second notification is not rejected (e.g., the second notification was postponed), however, method 300 proceeds to 315 (see FIG. 3A) and includes determining if the first ultrasound protocol is completed, as described above. As will be elaborated below, the system may automatically prompt the user to perform the second protocol after the first protocol is completed to further evaluate or verify the postponed detected potential abnormality.

Returning to 328, if the second notification is accepted, method 300 proceeds to 334 and includes generating the report regarding the detected potential abnormality. The report includes the type of potential abnormality detected, its location, measurements and or other quantifications (if available), and the suggested action for verifying (e.g., confirming) the potential abnormality. The report may also include annotated ultrasound images that indicate the position of the potential abnormality in the relevant views. In some examples, the suggested action includes proposing additional acquisition(s) using the first ultrasound protocol to verify the potential abnormality, as optionally indicated at 336. In other examples, the suggested action additionally or alternatively includes proposing additional acquisition(s) using the second ultrasound protocol to verify the potential abnormality, as optionally indicated at 338. The second ultrasound protocol includes views and/or imaging modes that are unable to be acquired using the first ultrasound protocol. As such, the report may include suggesting a view that is not part of the first ultrasound protocol, and thus, the second ultrasound protocol may be proposed and tailored to the patient and the potential abnormality to be detected.

When the report is generated responsive to the first notification being accepted at 316 or responsive to the second notification being accepted at 328, the report may be immediately generated upon receiving the acceptance (see FIG. 3C). In such examples, the first ultrasound protocol is automatically paused by the system and automatically resumes once the report on the potential (e.g., suspected) abnormality is completed. By contrast, generation of the report may be delayed until after the first ultrasound protocol is completed (e.g., as determined at 315) if the notification was postponed (e.g., the first notification is postponed or rejected at 318 and not rejected at 321, or the second notification is not accepted at 328 and not rejected at 331) or the "do not disturb" option was selected (e.g., at 311). Thus, the report may be generated before the first ultrasound protocol is fully completed or after the first ultrasound protocol is completed depending on settings of the notification system and/or inputs received from the operator.

As a first illustrative example, the system may detect a potential thrombus in the left atrium in a two-chamber view (e.g., at 308) that may or may not be intended to identify a potential thrombus, and responsive to one of the first notification and the second notification being accepted or postponed, the system generates a report including suggestions for additional left atrium focus images to acquire to confirm the thrombus and determine its size and mobility. As mentioned above, the system may automatically pause the first ultrasound protocol and immediately generate the report responsive to the first or second notification being accepted and automatically resume the first ultrasound protocol once the report on the suspected abnormality is completed. By contrast, the report may be generated after the first ultrasound protocol is completed responsive to the first notification and/or the second notification being postponed. The left atrium focus images may not normally be acquired using the first ultrasound protocol had the abnormality not been detected.

As a second illustrative example, the system may detect a potential motion abnormality upon analyzing the four-chamber views and the two-chamber view combined (e.g., at 308). For example, the system may identify potential reduced motion in three segments, which may suggest a potential myocardial infarction. Responsive to one of the first notification and the second notification being accepted, the system generates a report including suggestions for performing a speckle tracking analysis as the second ultrasound protocol to confirm the motion abnormality before the first ultrasound protocol is completed. Responsive to the first notification being postponed, the second notification being postponed, and/or the "do not disturb" option being selected, the system generates the report including suggestions for performing the speckle tracking analysis after the first ultrasound protocol is completed.

As a third illustrative example, the system may detect a potential stroke volume abnormality (e.g., at 308). For example, after analyzing all of the left ventricle and right ventricle images, the system may determine that there is a significant difference in the stroke volume between the left ventricle and the right ventricle, which may be indicative of a shunt or valvular leakage. Responsive to one of the first notification and the second notification being accepted or postponed, the system generates a report (either during the first protocol while it paused if the notification is accepted or after the first protocol completes if the notification is postponed) including a protocol for identifying the leakage as the second ultrasound protocol. Alternatively, the system generates the report including the protocol for identifying the leakage as the second ultrasound protocol upon completion of the first protocol responsive to the "do not disturb" option being selected.

At 340, method 300 includes displaying the ultrasound image(s) with the generated report. Displaying the ultrasound image(s) with the generated report includes outputting the generated ultrasound image(s) and the generated report on the display device. That is, the pixel parameter values calculated at 306 are included in the displayed image(s) output to the display device, which may be annotated with the information included in the report generated at 334. Additionally, the displayed report may include options or commands for performing the suggested action for verifying the potential abnormality. The operator may select, deselect, or otherwise interact with the options or commands to perform the suggested action for verifying the potential abnormality. Further, the system may prompt the operator to indicate whether the potential abnormality is a true abnormality or not, such as by prompting the operator to manually input the results of the suggested action and/or by using the artificial intelligence system to confirm the potential abnormality in the additional acquisitions. The generated report is also saved and/or archived (e.g., as a structured report in a PACS system) so that it may be retrieved and used to generate an official, physician-signed report that may be included in the patient's medical record (e.g., the EHR). Following 340, method 300 returns.

In this way, the system automatically detects the potential abnormality, but does not display all of the information regarding the potential abnormality until prompted by the operator. As a result, the operator is not subjected to potentially large amounts of information regarding the potential abnormality when it may be distracting. Further, by suggesting actions for verifying the potential abnormality, a likelihood of the abnormality being accurately identified or dismissed is increased. Additionally, a variability between operators in abnormality detection accuracy and frequency is decreased. Further still, either contemporaneous with showing the first notification or upon receiving a postponement, the notification system may include an option (e.g., the "do not disturb" option) for automatically postponing or dismissing all further detected abnormalities during the first protocol. In such an example, however, the system may still continue logging all detected potential abnormalities in the log file for review and follow up action after the first protocol is completed.

Next, FIGS. 4A-4E show example display outputs during an ultrasound exam of a patient. In particular, FIGS. 4A-4E show an illustrative example sequence of display outputs that may occur responsive an artificial intelligence system detecting a potential abnormality in the patient, such as described above with respect to FIGS. 3A-3C. However, it may be understood that additional display outputs may be included in the sequence between the example display outputs shown. The display outputs are shown on a display device 401, which may be the display device 118 of FIG. 1 or the display device 233 of FIG. 2, for example.

Figure 4A:
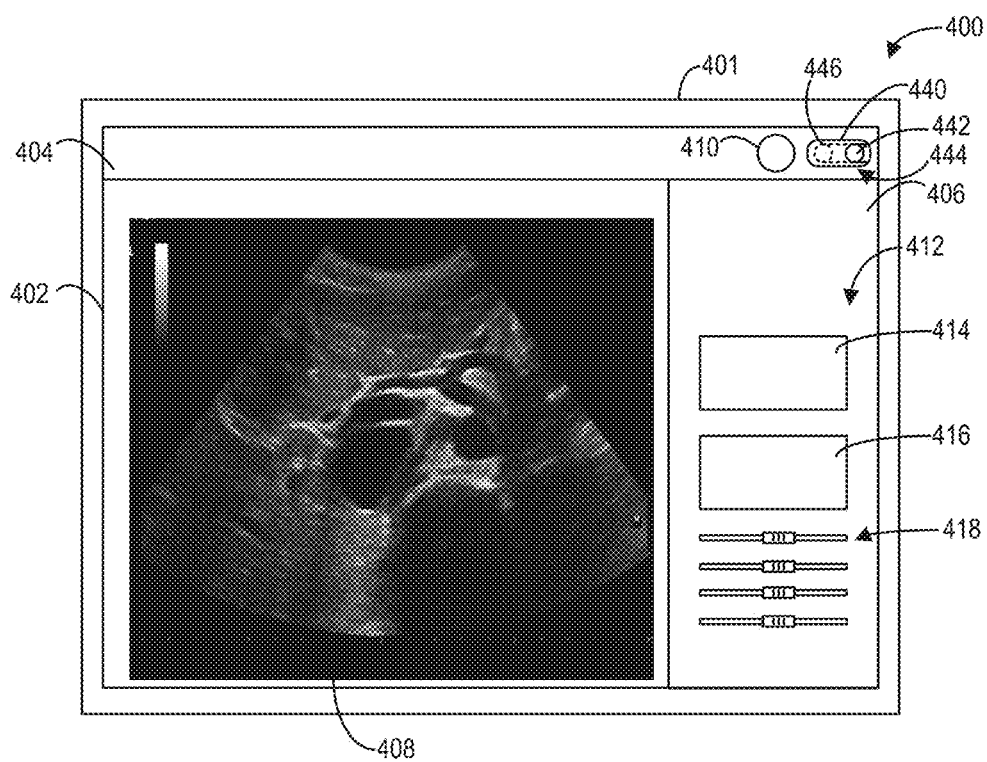
FIGS. 4A-4E show example display outputs of a user interface having a notification system, according to an embodiment.

Turning first to FIG. 4A, a first example display output 400 on a display area 402 of the display device 401 is shown. In the embodiment shown, the display area 402 includes a title bar 404 and a sidebar 406, although other organizations of the display area 402 are also possible, and displays an ultrasound image 408. The title bar 404 may include information regarding the date and time, ultrasound exam settings, and a title of the exam, for example. A notification center icon 410 for selecting and opening a notification center is also positioned in the title bar 404, while the sidebar 406 includes a plurality of user-selectable virtual inputs 412. The plurality of user-selectable virtual inputs 412 may include, as non-limiting and illustrative examples, a virtual button 414 for selecting a first imaging mode, a virtual button 416 for selecting a second imaging mode, a plurality of sliders 418 for adjusting settings, and so on. Further, the title bar 404 includes a "do not disturb" toggle switch 440 having a selector 442. In the example shown in FIGS. 4A-4E, the selector 442 is in an "off" position 444 (in contrast to an "on" position 446 shown in dashed lines). With the selector 442 in the "off" position 444, a "do not disturb" option is not selected, as described above with respect to 311 of FIG. 3A, and thus, notifications regarding the potential abnormality will be output on the display area 402 as the potential abnormalities are detected. It may be appreciated that additional information as well as additional or alternative user-selectable user inputs may be displayed in the display area 402. The plurality of user-selectable virtual inputs 412 may be selected or controlled responsive to the operator pressing and/or dragging a finger, stylus, cursor, or other suitable probe for interacting with the information shown on the display device 401. For example, the operator may position the cursor at a slider of the plurality of sliders 418, perform a selection action (e.g., depress a mouse button or tap a touchpad) to select the slider, and drag the slider to increase or decrease a parameter associated with the slider. As another example, the operator may move the selector 442 of the "do not disturb" toggle switch 440 to the "on" position 446 by pressing and/or dragging the selector 442 via a finger, stylus, cursor, or other suitable probe.

Figure 4B:
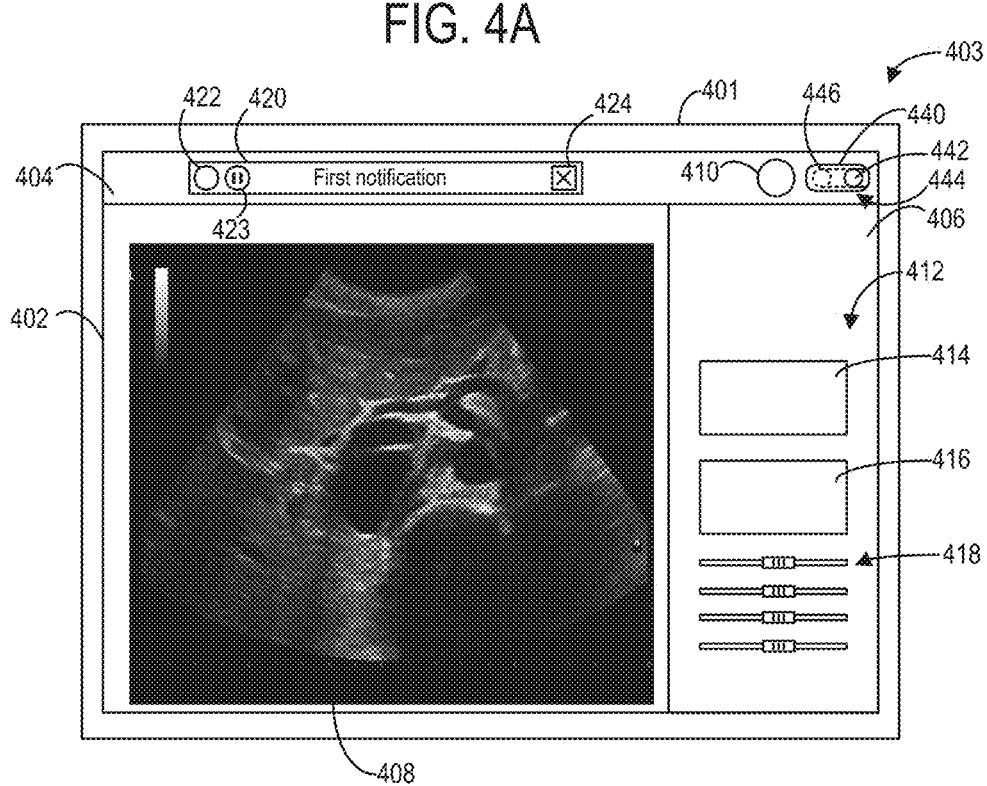

Continuing to FIG. 4B, a second example display output 403 is shown on the display area 402 of the display device 401. The second example display output 403 is substantially identical to the first example display output 400 shown in FIG. 4A except for the addition of a first notification message 420. The first notification message 420 is positioned within the title bar 402. As such, the first notification message 402 does not hide, obscure, or overlap with the ultrasound image 408 or any of the plurality of user-selectable virtual inputs 412 positioned within the sidebar 406. Further, the first notification message 420 does not hide, obscure, or overlap with the notification center icon 410.

As elaborated above with respect to FIGS. 3A-3C, the first notification message 420 is displayed in the display area 402 of the display device 401 responsive to the artificial intelligence system detecting the potential abnormality and includes information about the potential abnormality. The first notification message 420 also includes an accept icon 422, a postpone icon 423, and a reject icon 424. Responsive to the accept icon 422 being selected (e.g., by the operator), additional information regarding the detected potential abnormality as well as the option to select an action for verifying the potential abnormality may be output to the display area 402, such as described above at 340 of FIG. 3C. Responsive to the postpone icon 423 being selected, the first notification message 420 is removed from the display area 402, and the additional information regarding the detected potential abnormality and the action for verifying the potential abnormality is not output to the display area 402 until a current protocol is completed. Responsive to the reject icon 424 being selected, the first notification message 420 is removed from the display area 402 without additional information and selectable actions being displayed in the display area 402, such as described above at 332 of FIG. 3B.

Figure 4C:
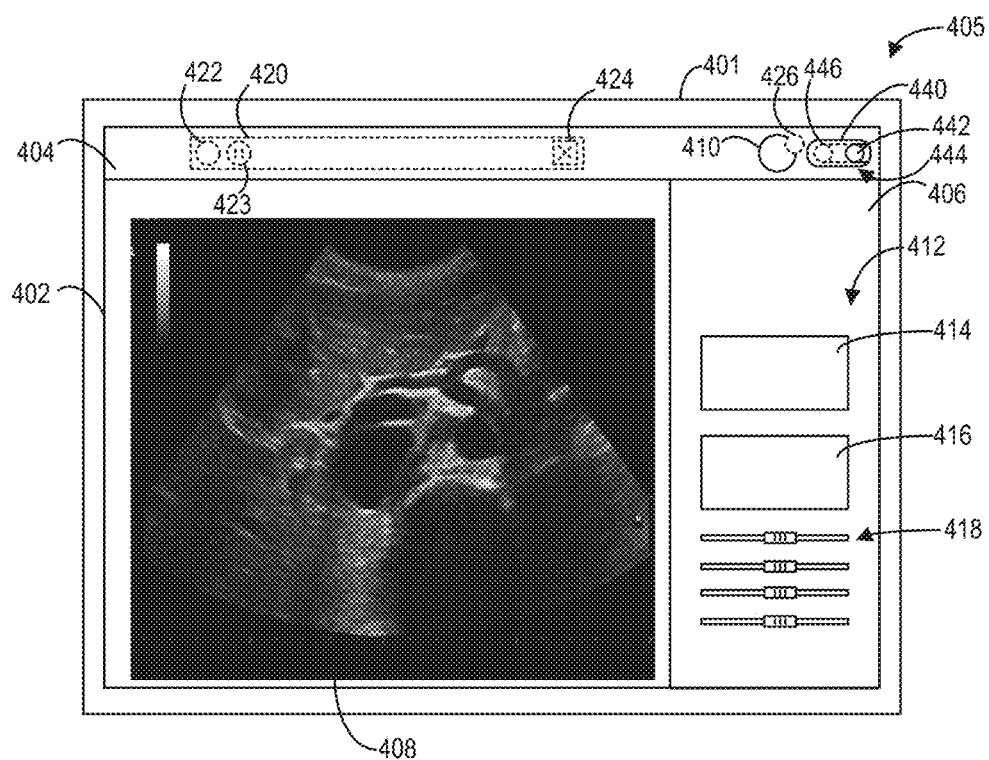

Continuing to FIG. 4C, a third example display output 405 is shown on the display area 402 of the display device 401. The third example display output 405 is substantially identical to the first example display output 400 shown in FIG. 4A and the second example display output 403 of FIG. 4B except for the differences described below. The third example display output 405 shows a transition period during which the first notification message 420 is removed from the display area 402 and a notification indicator 426 is output at the notification center icon 410. For example, the third example display output 405 may correspond to reaching a threshold duration for displaying the first notification message 420 without the operator selecting the accept icon 422, the postpone icon 423, or the reject icon 424, as elaborated above with respect to FIG. 3B. The first notification message 420 and the notification indicator 426 are shown in dashed lines to represent the transitional nature of the third example display output 405. For example, the first notification message 420 may be removed from the display area 402 via a transition effect or animation, such as fade out transition, a dissolve transition, a wipe transition, a push transition, or another type. Similarly, the notification indicator 426 may be added to the display area 402 via the same or different transition effect or animation. However, in other examples, the first notification message 420 may instantaneously disappear from the display area 402, and the notification icon 426 may instantaneously appear at the notification center icon 410 (e.g., the transitional third example display output 405 may not be included in the sequence).

Figure 4D:
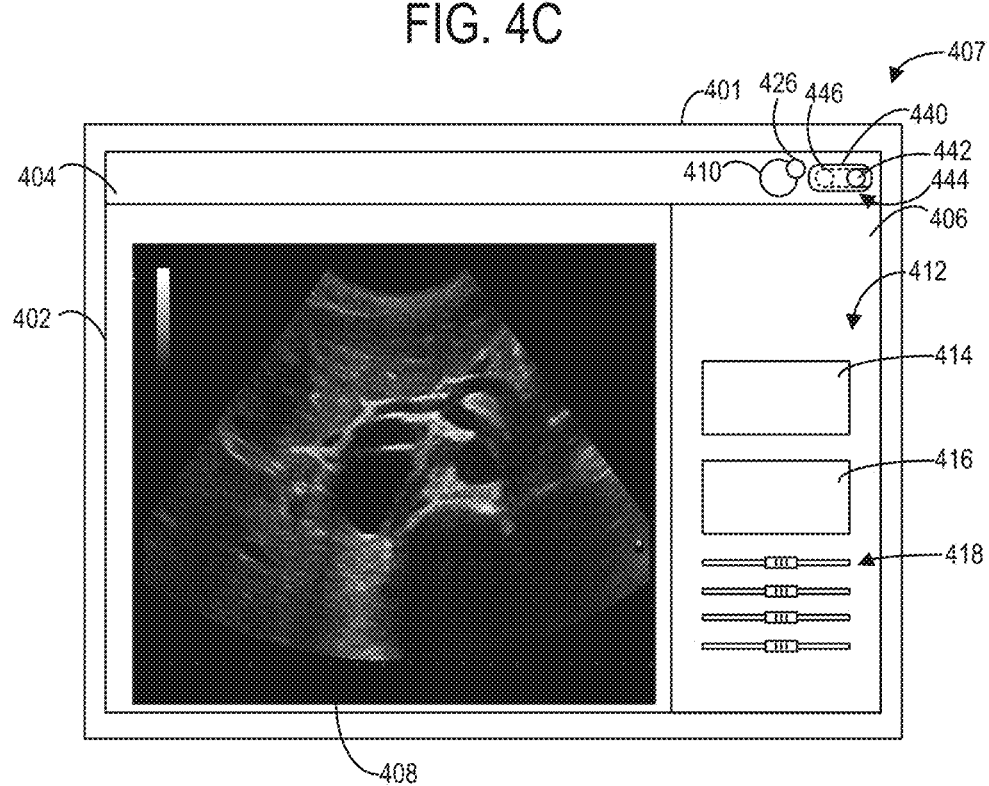

FIG. 4D shows a fourth example display output 407. The fourth example display output 407 is substantially identical to the first example display output 400 shown in FIG. 4A, the second example display output 403 shown in FIG. 4B, and the third example display output 405 shown in FIG. 4C except for the differences described below. Specifically, the transition represented in the third example display output 405 of FIG. 4C is completed in the fourth example display output 407. The notification indicator 426 is present at the notification center icon 410, indicating that there are unresolved notifications at the notification center. Further, the first notification message 420 shown in FIGS. 4A-4C is fully removed from the display area 402 and is not shown in the fourth example display output 407.

Figure 4E:
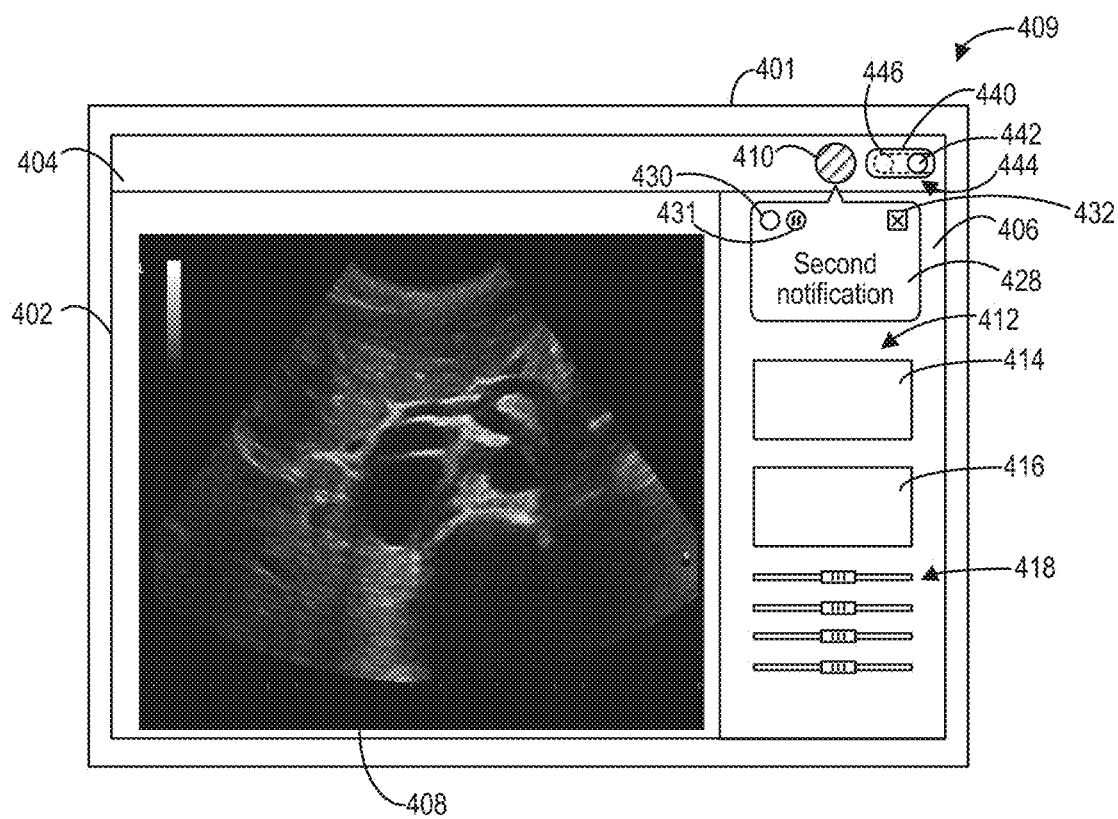

Continuing to FIG. 4E, a fifth example display output 409 is shown. The fifth example display output 409 is substantially identical to the first example display output 400 shown in FIG. 4A, the second example display output 403 shown in FIG. 4B, the third example display output 405 shown in FIG. 4C, and the fourth example display output 407 shown in FIG. 4D except for the differences described below.

In the fifth example display output 409, the notification center icon 410 has been selected, as represented by a shaded fill. Because the notification center icon 410 has been selected (e.g., by the operator), a second notification message 428 is output in the display area 402. As described above with respect to FIG. 3B, the second notification message 428 may include at least the information conveyed in the first notification message 420 shown in FIG. 4B. In the example shown in FIG. 4E, the second notification message 428 extends downward from the notification center icon 410 and into the sidebar 406. Further, the second notification message 428 does not hide, obscure, or overlap with the ultrasound image 408 or any of the plurality of user-selectable virtual inputs 412. Thus, the operator may continue to access the user-selectable virtual inputs 412 and continue observing the ultrasound image 408 even while the second notification message 428 is displayed.

The second notification message 428 also includes an accept icon 430, a postpone icon 431, and a reject icon 432. Responsive to the accept icon 430 being selected (e.g., by the operator), additional information regarding the detected potential abnormality as well as the option to select an action for verifying the potential abnormality may be output to the display area 402, such as described above at 340 of FIG. 3C. Responsive to the postpone icon 431 being selected, the second notification message 428 is removed from the display area 402, and the additional information regarding the detected potential abnormality and the action for verifying the potential abnormality is not output to the display area 402 until the current protocol is completed. Responsive to the reject icon 432 being selected, the second notification message 428 is removed from the display area 402 without additional information and selectable actions being displayed in the display area 402, such as described above at 332 of FIG. 3B. However, the second notification message 428 may remain displayed in display area 402 until one of the accept icon 430, the postpone icon 431, and the reject icon 432 is selected, at least in some examples.

In this way, a processor may automatically detect a potential abnormality by evaluating medical images from a patient using recognition and classification algorithms. The processor may alert a healthcare professional to the detected potential abnormality via a user-centric notification method. As a result, an amount of time the healthcare professional spends reviewing the medical images may be reduced, enabling the healthcare professional to focus on patient care and comfort. Further, by automatically detecting the potential abnormality and alerting the healthcare professional in real-time while a scan is performed, the healthcare professional is able to adapt the scan protocol, which may be personalized for the patient using suggestions generated by the processor based on the detected potential abnormality, to determine whether the potential abnormality is present (e.g., a verified abnormality) or not. Further still, machine learning may be applied to the recognition and classification algorithms to further refine detection models as more training data becomes available, thereby increasing an accuracy of the recognition and classification algorithms.

A technical effect of automatically detecting a potential abnormality in medical images and proposing additional acquisition protocols based on the detected potential abnormality is that an accuracy and frequency at which abnormalities are detected may be increased. A technical effect of notifying an operator to a detected potential abnormality without obscuring exam controls and exam data is that operator distraction may be decreased while an amount of information conveyed to the operator may be increased.

In one embodiment, a method comprises: acquiring medical imaging data according to a first imaging protocol; detecting a potential abnormality by evaluating the acquired medical imaging data with an artificial intelligence system; and outputting a first notification regarding the potential abnormality to a display, the first notification including an option to accept the first notification and an option to reject the first notification. A first example of the method further comprises, responsive to a selection of the option to reject the first notification, removing the first notification from the display; and responsive to a selection of the option to accept the first notification, outputting a report regarding the detected potential abnormality to the display. In a second example of the method, which optionally includes the first example, the report regarding the detected potential abnormality includes guidance for verifying the detected potential abnormality using the first imaging protocol. In a third example of the method, which optionally includes one or both of the first and second examples, the report regarding the detected potential abnormality includes guidance for verifying the detected potential abnormality using a second imaging protocol, the second imaging protocol including at least one of a view and an acquisition mode that is not included in the first imaging protocol, and outputting the report pauses the first imaging protocol until the second imaging protocol is completed. In a fourth example of the method, which optionally includes any or all of the first through third examples, the first notification further includes an option to postpone the first notification. A fifth example of the method optionally includes any or all of the first through fourth examples and further comprises: responsive to none of the option to accept the first notification, the option to postpone the first notification, and the option to reject the first notification being selected after a threshold duration has elapsed since outputting the first notification to the display, removing the first notification from the display and storing information given by the first notification at a notification center. In a sixth example of the method, which optionally includes any or all of the first through fifth examples, storing the information given by the first notification at the notification center includes outputting an indicator on the display at an icon for the notification center, and the method further comprises: responsive to the notification center being selected, outputting a second notification to the display, the second notification including the information given by the first notification and further including an option to accept the second notification, an option to postpone the second notification, and an option to reject the second notification; and responsive to the option to accept the second notification being selected, outputting the report regarding the detected potential abnormality to the display. A seventh example of the method optionally includes any or all of the first through sixth examples and further comprises: responsive to a selection of the option to postpone the first notification, outputting the report regarding the detected potential abnormality to the display upon completion of the first imaging protocol. In an eighth example of the method, which optionally includes any or all of the first through seventh examples, outputting the first notification is responsive to an off state of a do not disturb setting. In a ninth example of the method, which optionally includes any or all of the first through eighth examples, the potential abnormality is a parameter of an anatomical feature imaged in the acquired medical imaging data that is at least one of outside of a standardized range and pathological, and detecting the potential abnormality by evaluating the acquired medical imaging data with the artificial intelligence system includes evaluating the acquired medical imaging data in real-time during the acquiring, the artificial intelligence system including one or more deep neural networks. In a tenth example of the method, which optionally includes any or all of the first through ninth examples, the medical imaging data includes at least one of ultrasound imaging data, magnetic resonance imaging data, computed tomography data, x-ray data, and positron emission tomography data.

In another embodiment, a method comprises: detecting a potential abnormality in an imaged region of a patient; receiving acceptance, postponement, or rejection of a notification regarding the potential abnormality; instantaneously outputting a report on the potential abnormality responsive to receiving the acceptance of the notification; delaying outputting the report on the potential abnormality responsive to receiving the postponement of the notification; and logging the detected potential abnormality without outputting the report responsive to receiving the rejection of the notification. In a first example of the method, receiving the acceptance, postponement, or rejection of the notification regarding the potential abnormality includes: outputting the notification to a display device, the notification including an acceptance input, a postponement input and a rejection input; receiving acceptance of the notification via the acceptance input; receiving postponement of the notification via the postponement input; and receiving rejection of the notification via the rejection input. In a second example of the method, which optionally includes the first example, detecting the potential abnormality in the imaged region of the patient includes: acquiring medical imaging data of the imaged region via an imaging protocol; and analyzing the medical imaging data for potential abnormalities via an artificial intelligence system. In a third example of the method, which optionally includes one or both of the first and second examples, analyzing the medical imaging data for potential abnormalities via the artificial intelligence system includes analyzing the medical imaging data in real-time during the acquiring, and outputting the notification to the display device includes outputting the notification in a region of the display device not overlapping controls for the acquiring. In a fourth example of the method, which optionally includes any or all of the first through third examples, analyzing the medical imaging data for potential abnormalities includes analyzing the medical imaging data after acquiring the medical imaging data. In a fifth example of the method, which optionally includes any or all of the first through fourth examples, delaying outputting the report on the potential abnormality responsive to receiving the postponement of the notification includes outputting the report after the imaging protocol is finished. In a sixth example of the method, which optionally includes any or all of the first through fifth examples, outputting the notification to the display is responsive to receiving selection of a notification center.

In another embodiment, a system comprises: an ultrasound probe; a display device; and a processor configured with instructions in non-transitory memory that, when executed, cause the processor to: acquire ultrasound data via the ultrasound probe according to a first imaging protocol; evaluate the ultrasound data with a deep neural network to detect an abnormality; and output an abnormality report on the display device responsive to detecting the abnormality and responsive to receiving acceptance of a notification. In a first example of the system, the abnormality report includes a type of the abnormality, a location of the abnormality, and additional views to be acquired using at least one of the first imaging protocol and a second imaging protocol, the second imaging protocol including a different imaging mode than the first imaging protocol, and the processor is further configured with instructions in the non-transitory memory that, when executed, cause the processor to: output the abnormality report on the display device responsive to detecting the abnormality, receiving postponement of the notification, and the first imaging protocol completing. In a second example of the system, which optionally includes the first example, the processor is further configured with instructions in the non-transitory memory that, when executed, cause the processor to output the notification at a pre-determined timing during the first imaging protocol or responsive to receiving a pre-defined input.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method, comprising:
acquiring, via a scanner, medical imaging data of a patient during an ultrasound exam of the patient conducted according to a first imaging protocol that includes one or more views to be obtained and one or more acquisition modes to be performed during the ultrasound exam to diagnose the patient;
detecting a potential abnormality by evaluating the acquired medical imaging data with an artificial intelligence system in real time while the ultrasound exam is still being conducted;
outputting a first notification regarding the potential abnormality to a display while the ultrasound exam is still being conducted, the first notification including a reduced amount of information regarding the potential abnormality, an option to accept the first notification, and an option to reject the first notification;
responsive to a selection of the option to accept the first notification, outputting a report regarding the detected potential abnormality to the display, the report including more information regarding the potential abnormality than the first notification, the more information including guidance for verifying the detected potential abnormality using a second imaging protocol, the second imaging protocol including at least one of a view and an acquisition mode that is not included in the first imaging protocol, and wherein outputting the report pauses the first imaging protocol until the second imaging protocol is completed; and
responsive to a selection of the option to reject the first notification, removing the first notification from the display.

2. The method of claim 1, further comprising receiving the selection of the option to accept the first notification via a user input and wherein the outputting is responsive to receiving the selection.

3. The method of claim 1, wherein evaluating the acquired medical imaging data with an artificial intelligence system in real time while the ultrasound exam is still being conducted comprises evaluating the acquired medical imaging data while additional medical imaging data is still being acquired via the scanner according to the first imaging protocol.

4. The method of claim 1, wherein the first notification further includes an option to postpone the first notification.

5. The method of claim 4, further comprising:
responsive to none of the option to accept the first notification, the option to postpone the first notification, and the option to reject the first notification being selected after a threshold duration has elapsed since outputting the first notification to the display, removing the first notification from the display and storing information given by the first notification at a notification center.

6. The method of claim 5, wherein storing the information given by the first notification at the notification center includes outputting an indicator on the display at an icon for the notification center, and the method further comprises:

responsive to the notification center being selected, outputting a second notification to the display, the second notification including the information given by the first notification and further including an option to accept the second notification, an option to postpone the second notification, and an option to reject the second notification; and responsive to the option to accept the second notification being selected, outputting the report regarding the detected potential abnormality to the display.

7. The method of claim 4, further comprising:

responsive to a selection of the option to postpone the first notification, outputting the report regarding the detected potential abnormality to the display upon completion of the first imaging protocol.

8. The method of claim 1, wherein outputting the first notification is responsive to an off state of a do not disturb setting.

9. The method of claim 1, wherein the potential abnormality is a parameter of an anatomical feature imaged in the acquired medical imaging data that is at least one of outside of a standardized range and pathological, and wherein detecting the potential abnormality by evaluating the acquired medical imaging data with the artificial intelligence system includes evaluating the acquired medical imaging data in real-time during the acquiring, the artificial intelligence system including one or more deep neural networks.

10. The method of claim 1, wherein the medical imaging data includes ultrasound imaging data, wherein the first protocol includes acquisition of a two-chamber view, wherein the artificial intelligence system is trained to detect a thrombus as the potential abnormality, and wherein the second protocol includes acquisition of additional left atrium focus images not included in the first protocol.

11. A system, comprising:
an ultrasound probe;
a display device; and
a processor configured with instructions in non-transitory memory that, when executed, cause the processor to:
acquire ultrasound data of a patient via the ultrasound probe during an ultrasound exam of the patient conducted according to a first imaging protocol that includes one or more views to be obtained and one or more acquisition modes to be performed to diagnose the patient;
evaluate, in real time while the ultrasound exam is still being conducted, the ultrasound data with a deep neural network to detect an abnormality; and
output an abnormality report on the display device responsive to detecting the abnormality and responsive to receiving acceptance of a notification, the notification including a reduced amount of information regarding the abnormality, the abnormality report including more information regarding the abnormality than the notification, including guidance for verifying the abnormality using a second imaging protocol, the second imaging protocol including at least one of a view and an acquisition mode that is not included in the first imaging protocol, and wherein outputting the abnormality report pauses the first imaging protocol until the second imaging protocol is completed.

12. The system of claim 11, wherein the processor is further configured with instructions in the non-transitory memory that, when executed, cause the processor to:

output the abnormality report on the display device responsive to detecting the abnormality, receiving postponement of the notification, and the first imaging protocol completing.

13. The system of claim 11, wherein the processor is further configured with instructions in the non-transitory memory that, when executed, cause the processor to output the notification at a pre-determined timing during the first imaging protocol or responsive to receiving a pre-defined input.

* * * * *